(12) United States Patent
Jackson

(10) Patent No.: US 6,664,404 B2
(45) Date of Patent: Dec. 16, 2003

(54) PROCESS FOR MANUFACTURING MONOESTERS OF POLYHYDROXYALCOHOLS

(75) Inventor: Graham Jackson, Reading (GB)

(73) Assignee: Infineum International Ltd. (GB)

(*) Notice: Subject to any disclaimer, the term of this patent is extended or adjusted under 35 U.S.C. 154(b) by 12 days.

(21) Appl. No.: 10/145,049

(22) Filed: May 14, 2002

(65) Prior Publication Data

US 2003/0013907 A1 Jan. 16, 2003

(30) Foreign Application Priority Data

May 23, 2001 (GB) ............................................. 0112557

(51) Int. Cl.$^7$ ................................................. C11C 1/00
(52) U.S. Cl. ....................................... 554/168; 554/169
(58) Field of Search ................................. 554/168, 169

(56) References Cited

U.S. PATENT DOCUMENTS 2,789,119 A * 4/1957 Sully ........................ 260/410.7

* cited by examiner

Primary Examiner—Deborah D. Carr

(57) ABSTRACT

An improved process for the manufacture of monoesters of polyhydroxyalcohols to high yields and high purities.

7 Claims, No Drawings

PROCESS FOR MANUFACTURING MONOESTERS OF POLYHYDROXYALCOHOLS

The present invention concerns an improved process for the preparation of monoesters of polyhydroxy alcohols and in particular for the preparation of polyhydroxy alcohol ester mixtures having high monoester contents. Such materials find application, for example, in the petroleum industry as additives for lubricants and fuels, or in the cosmetics or foods industries.

Fatty acid esters of polyhydroxy alcohols are well known in the art. Such materials may principally be manufactured by two routes:

a direct ('esterification') reaction between acid and polyhydroxy alcohol transesterification of a fatty acid ester with the polyhydroxy alcohol.

In both routes, the product of reaction is typically a complex mixture of esters, a result of the number of possible esterification sites on the alcohol and complex equilibria between individual ester isomers and between mono- and poly-esters in the product mix.

For certain applications, particular ester structures are particularly sought. In the petroleum industry, fatty acid monoesters of polyhydroxy alcohols such as pentaerythritol, sorbitol and particularly glycerol are particularly effective in certain applications. There thus exists a continual need for processes which preferentially synthesise the desired ester(s) to the extent that expensive post reaction separation processes become unnecessary.

U.S. Pat. No. 2,789,119 describes a process for the preparation of monoglycerides for naturally occurring fatty oils, fats or artificially prepared esters, involving the use of tertiary butyl alcohol as reaction medium. The reaction is performed at temperatures of up to 40° C. in the presence of alkaline catalyst and results in apparent monoester purities of up to 91% (Example 2) after several days reaction time. Following reaction, the desired monoester is removed by crystallisation where the physical properties of the ester permit. Unreacted glycerol is removed by water washing, the glycerol being extracted by and removed with the aqueous phase.

As the examples of U.S. Pat. No. 2,789,119 indicate, separation of the desired monoesters by crystallisation is a lengthy process, taking several days (Examples 2 and 3). Although a high yield is obtained, the process is thus uneconomic. Higher purities of the monostearate were also obtained relative to the more soluble monooleate ester.

There remains a need in the art for a process which proceeds on an economic time scale and which permits the preparation of monoesters of polyhydroxy alcohols, particularly monoesters of unsaturated acids and polyhydroxy alcohols such as glycerol, to both high yields and purities.

The present invention accordingly provides a process for the preparation of monoesters of one or more polyhydroxy alcohols, comprising:

| | |
|---|---|
| (i) | reacting the or each polyhydroxy alcohol with a glyceride ester composition derived from a natural or synthetic source, in the presence of tertiary butanol or tertiary amyl alcohol as reaction medium, and a catalyst; |
| (ii) | if necessary, neutralising the catalyst; |
| (iii) | removing the tertiary butanol or tertiary amyl alcohol; and |
| (iv) | removing the unreacted polyhydroxy alcohol and any liberated glycerol from the product mixture; | characterised in that in the reaction (i) the polyhydroxy alcohol is present in mass excess relative to the glyceride ester composition: the mass ratio of reaction medium to polyhydroxy alcohol is at least 0.8:1 in the case of tertiary butanol or at least 1.3:1 in the case of tertiary amyl alcohol; the reaction is carried out at a temperature at least equal to the reflux temperature of the reaction medium and at a pressure exceeding 1 bar; and the catalyst is selected from basic salts of Group I and Group II metals and non-metallic nitrogenous bases.

The process of this invention provides a high yield of the desired monoester to high purity in the product mix. In particular, it avoids the lengthy crystallisation period of U.S. Pat. No. 2,789,119 through the use of an excess of the polyhydroxyalcohol reactant. The preferred temperature and pressure conditions, and choice of catalyst, also contribute to achieving high yields in an economic reaction time.

High yield processes for the preparation of monoesters also exhibit the secondary problem of emulsification of glycerol liberated from the glyceride ester reactant or, if glycerol is also used as the polyhydroxyalcohol reactant, from unreacted excess starting material. Monoesters of polyhydroxyalcohols show a marked tendency to emulsify glycerol within the ester product phase. As the yield of monoesters increases, this secondary problem also increases to the point where significant glycerol remains within the ester phase and cannot be removed by the conventional water washing technique expounded in U.S. Pat. No. 2,789,119. Where glycerol also comprises the polyhydroxyalcohol reactant, recycling of the glycerol is also rendered less economic by the need to recover it from a water phase.

In a preferred embodiment, the process of the present invention is further characterised by the additional feature of the alcohol removal step (iv) being conducted by low residence time evaporation, and preferably by thin film evaporation. This evaporation step permits the effective removal of excess glycerol, reducing the associated debits of free glycerol in the ester product without the associated emulsification from a water wash.

The process will now be described in more detail, as follows.

The Process Conditions

In the process of the invention, the polyhydroxyalcohol is preferably present in considerable excess, as measured by the mass ratio of alcohol to glyceride ester being at least 1.5:1, and preferably at least 2:1.

A minimum quantity of reaction medium (tertiary butanol or tertiary amyl alcohol) is required relative to the quantity of polyhydroxyalcohol, to ensure homogeneity and maximal yield of monoester. The selection of reaction medium (ie. tertiary butanol or tertiary amyl alcohol) depends on practical factors such as solvency and handleability at ambient temperature.

The reaction (i) is preferably carried out at temperatures exceeding 90° C., more preferably exceeding 125° C., such as exceeding 150° C., and most preferably exceeding 170° C. The reaction is preferably carried out at pressures exceeding 3 bars, and more preferably at pressures exceeding 7 bars.

The catalyst for reaction (i) is chosen from the following basic catalyst groups:

1) basic salts of Group I and Group II metals, such as lithium, sodium, potassium, calcium and magnesium salts of, for example, carbonate, hydroxide, oxide, alkoxide or acetate anions. In particular, the catalyst may be selected from lithium carbonate, lithium hydroxide, sodium carbonate, sodium methoxide, potassium t-butoxide, calcium oxide, sodium hydroxide and sodium acetate;

2) non-metallic nitrogenous bases, preferably selected from DBU (1,8-diazabicyclo[5.4.0]undec-7-ene), tetraalkylammonium hydroxides, choline hydroxide, choline bicarbonate, and other strong nitrogenous bases. Other non-metallic bases have been found to be less effective, whilst DBU is most preferred base.

Neutralisation of a catalyst from Group 1 above will usually be necessary. However, catalysts from Group 2 above may be employed without neutralisation and recycled to allow repeated usage. DBU is particularly advantageous in this respect.

The choice of catalyst is important to the process. In particular, other catalysts such as acidic catalysts will lead to re-equilibration of the ester product mixture and loss of high monoester content.

In the preferred embodiment of the process, the thin film evaporation step is preferably conducted at a temperature of 160 to 200° C. and, preferably, at a reduced pressure of 0.5 to 40 mbar. A short residence time is preferred to minimise the possibility of ester decomposition in the evaporator.

The Reactants

In all embodiments of the process, the term polyhydroxy alcohol is used to describe a compound having more than one hydroxy group. It is preferred that the polyhydroxy alcohol has at least three hydroxy groups and more prefered that the alcohol be removable from the product mixture by distillation.

Example of polyhydroxy alcohols having at least three hydroxy groups are those having 3 to 10, preferably 3 to 6, more preferably 3 to 4 hydroxy groups and having 2 to 90, preferably 2 to 30, more preferably 2 to 12 and most preferably 3 to 4 carbon atoms in the molecule. Such alcohols may be aliphatic, saturated or unsaturated, and straight chain or branched, or cyclic derivatives thereof. Saturated, aliphatic, straight chain alcohols are preferred.

Advantageously, the polyhydroxy alcohol is glycerol or trimethylol propane. Most preferably, the alcohol is glycerol.

The glyceride ester reactant composition is preferably derived from a natural source such as a vegetable oil. Preferred vegetable oils are triglycerides of monocarboxylic acids, for example acids containing 10–25 carbon atoms, and typically have the general formula shown below

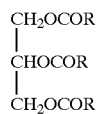

where R is an aliphatic radical of 10–25 carbon atoms which may be saturated or unsaturated.

Generally, such oils contain glycerides of a number of acids, the number and kind varying with the source vegetable of the oil.

Examples of oils are rapeseed oil, coriander oil, soyabean oil, cottonseed oil, sunflower oil, castor oil, olive oil, peanut oil, maize oil, almond oil, palm kernel oil, coconut oil and mustard seed oil. Rapeseed oil, which is a mixture of fatty acids partially esterified with glycerol, is preferred as it is available in large quantities and can be obtained in a simple way by pressing from rapeseed.

Alternatively, the glyceride esters may be derived from an animal source such as beef tallow oils or fish oils.

The glyceride ester composition, and in particular the composition derived from a vegetable source, comprises triglycerides of saturated and unsaturated fatty acids with 12 to 22 carbon atoms, for example of lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid or erucic acid, which have an iodine number from 50 to 150, especially 90 to 125. Oils predominating in glycerides of one or more of oleic, linoleic, linolenic and erucic acids are preferred.

The invention will now be described by way of examples as follows:

EXAMPLE 1

Preparation of Glycerol Monoester

A mixture of vegetable oil (1.66 Kg), glycerol (3.51 Kg), t-butanol (3.32 Kg) and lithium carbonate (1.69 g) was heated at 175° C. with stirring and under nitrogen for 4 hours in an autoclave at a pressure of 10 bar (150 psi). The reactor was then allowed to cool to room temperature. To a 400 g sample of the reaction mixture was added 0.114 g oxalic acid in order to neutralise the catalyst. The t-butanol was removed by distillation under reduced pressure. The glycerol was then removed by distillation in a thin-film evaporator at a temperature of 180° C. and a reduced pressure of 1 mbar. The residence time of the mixture was kept short in order to minimise any tendency of the monoester to revert to the di-and tri-esters and also to keep the residual glycerol in the product as low as possible, preferably below 1.5%. This gave a >90% yield of glycerol monoesters in the product as determined by the periodate method of analysis.

EXAMPLE 2

Illustration of Emulsification with Water Washing

A further 200 g sample of the reaction mixture from Experiment 1 was similarly neutralised and the t-butanol removed by distillation. To the remaining material was added water in increasing amounts from 0.5 ml to 20 ml in order to try to separate the glycerol monoesters from a glycerol/water phase. In all proportions the resulting mixture gave emulsions that were very difficult, if not impossible, to separate.

EXAMPLES 3 & 4

Further Examples of the Invention

The recovered glycerol and t-butanol from Experiment 1 were used without further treatment in a second reaction with fresh vegetable oil and fresh lithium carbonate. This reaction was worked-up in the same way to give glycerol monoester in >90% yield as determined by the periodate method of analysis (Example 3).

Another reaction similar to that in example 1 was performed using DBU (1,8-diazabicyclo[5.4.0]under-7-ene) (7.55 g) as the catalyst in place of the lithium carbonate. A 400 g sample was worked up in the same way adding in this case, 0.212 g oxalic acid to neutralize the catalyst), to give glycerol monoester in >90% yield as determined by the periodate method of analysis (Example 4).

EXAMPLE 5

Preparation of Glycerol Monoester Using t-amyl Alcohol as Solvent

A mixture of vegetable oil (33 g), glycerol (70 g), t-amyl alcohol (96 g) and lithium carbonate (37 mg) was heated at 180° C. and about 7.5 bar for 4 hours. The mixture was then cooled to about 50° C. and to it was added 195 mg p-toluenesulphonic acid in order to neutralize the catalyst. The t-amyl alcohol was evaporated under reduced pressure and to the residue was added toluene (150 ml). The resultant mixture formed 2 phases—the glycerol esters being in the upper phase and most of the excess glycerol being in the lower phase. The lower phase was removed and the toluene from the upper phase was evaporated under reduced pressure to give a product that contained the glycerol monoesters in >90% yield as determined by the periodate method of analysis.

The usefulness of the monoester product of the process is illustrated by the following example, in which a 92% monoester product obtained by the process was employed as a lubricity additive for low sulphur diesel fuel.

Concern for the environment has resulted in moves to significantly reduce the noxious components in emissions when fuel oils are burnt, particularly in engines such as diesel engines. Attempts are being made, for example, to minimise sulphur dioxide emissions. As a consequence, attempts are being made to minimise the sulphur content of fuel oils. For example, although typical diesel fuels oils have in the past contained 1% by weight or more of sulphur (expressed as elemental sulphur) it is now considered desirable to reduce the sulphur level to 0.05% by weight and, advantageously, to less than 0.01% by weight, particularly less than 0.001% by weight.

Additional refining of fuel oils, necessary to achieve these low sulphur levels, often results in reductions in the level of naturally-occuring polar components. In addition, refinery processes can reduce the level of polynuclear aromatic compounds present in such fuel oils.

Reducing the level of one or more of the sulphur, polynuclear aromatic or polar components of diesel fuel oil can reduce the solubility of the oil to lubricate the injection system of the engine so that, for example, the fuel injection pump of the engine fails relatively early in the life of an engine. Failure may occur in fuel injection systems such as high pressure rotary distributor pumps, in-line pumps and injectors. The problem of poor lubricity in diesel fuel oils is likely to be exacerbated by the future engine developments aimed at further reducing emissions, which will have more exacting lubricity requirements than present engines. For example, the advent of high pressure unit injectors is anticipated to increase the fuel oil lubricity requirement.

Similarly, poor lubricity can lead to wear problems in other mechanical devices dependent for lubrication on the natural lubricity of fuel oil.

Glycerol esters have been described for use in low sulphur diesel fuels for restoring the lubricity characteristics of such fuels to acceptable levels. The products of the process of the invention show particularly good performance as lubricity improvers, especially without the need for post-reaction purification or separation processes.

Furthermore, the inventors have found that within a monoester product mixture, which contains a variety of monoester isomers depending upon the position of the ester group within individual molecules, different isomers have different relative efficacies in this application. Thus, monoester isomers wherein a terminal hydroxy group of the polyhydroxy alcohol reactant has been esterified show enhanced lubricity performance over isomers wherein an internal hydroxy group has been esterified. Thus, for example where the polyhydroxyalcohol is glycerol, the glycerol-1-monooleate shows enhanced lubricity performance when compared to the analogous glycerol-2-monooleate:

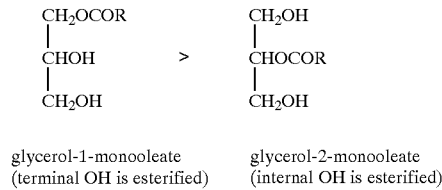

glycerol-1-monooleate (terminal OH is esterified)    glycerol-2-monooleate (internal OH is esterified)

EXAMPLE 6

Lubricity Performance of the Monoester

A test that can be used to demonstrate an improvement in fuel lubricity according to this invention is the High Frequency Reciprocating Rig test (or "HFRR"), described in the standard test methods CEC PF 06-T-94 or ISO/TC22/SC7/SG6/N188.

In brief, the HFRR test measures the wear scar diameter produced on reciprocating metal surfaces lubricated by means of the fuel, and mimics the wear observed in a diesel engine fuel injection pump. In the test, smaller wear scars indicate less wear, ie improved lubricity.

A product of the process of the invention (92% glycerol monoester, derived from rapeseed oil reactant) was HFRR tested in a low sulphur diesel fuel. Compared to the untreated fuel, a clear reduction in wear scar (indicating an enhancement of fuel lubricity) was see when the fuel contained 125 ppm (parts per million by weight, per weight of fuel) of the product.

| Fuel | Average HFRR wear scar diameter ($\mu$m) |
|---|---|
| Base Fuel | 630 $\mu$m |
| Fuel + 125 ppm product of the invention | 366 $\mu$m |

The product of the process may be used as an additive for fuel oils by its incorporation into a composition itself comprising one or more additives for fuel oils. Such incorporation may be achieved by blending or mixing, either with an existing composition or with the components thereof, to produce an additive composition. The term 'incorporation' within the meaning of this specification extends not only to the physical mixing of the product with other materials, but also to any physical and/or chemical interaction which may result upon introduction of the product or upon standing.

Many fuel oil additives are known in the art and may be used to form the composition into which the product is incorporated. Such additives include for example the following: detergents, antioxidants, corrosion inhibitors, dehazers, demulsifiers, metal deactivators, antifoaming agents, cetane improvers, combustion improvers, dyes, packages compatibilisers, further lubricity additives and antistatic additives. Cold flow-improving additives may also be present.

A concentrate may be obtained by incorporating the product of the additive composition into a mutually-compatible solvent therefor. The resulting mixture may be either a solution or a dispersion, but is preferably a solution. Suitable solvents include organic solvents including hydrocarbon solvents, for example petroleum fractions such as naphtha, kerosene, diesel and heating oil; aromatic hydrocarbons such as aromatic fractions, eg, those sold under the 'SOLVESSO' tradename; and paraffinic hydrocarbons such as hexane and pentane and isoparaffins.

Further solvents include oligomers and hydrogenated oligomers of alkenes such as hydrogenated decene-1 dimer or trimer. Also useful are alcohols and esters especially high alcohols such as liquid alkanols having at least eight carbon atoms. An especially useful solvent is isodecanol. Mixtures of such solvents maybe used in order to produce a mutually-compatible solvent system.

The concentrate may contain up to 80% by weight, for example 50%, of solvent.

The concentrate is particularly convenient as a means for incorporating the product into fuel oil where despite the presence of the product, the co-presence of other additives in the composition demands an amount of solvent in order to impart handleability. However, concentrates comprising the product as sole additive may also be used, especially where small quantities of additives are required and the equipment present for introduction of the additive lacks the necessary accuracy to measure or handle such small volumes.

A further aspect of this invention is therefore the use of the product, or the additive composition or concentrate, in a liquid hydrocarbon middle distillate fuel oil, having a sulphur concentration of 0.05% by weight or less, per weight of fuel, particularly to improve the lubricity thereof. This invention also provides a method for improving the lubricity of a liquid hydrocarbon middle distillate fuel oil having a sulphur concentration of 0.05% by weight of fuel, comprising the addition thereto of the additive composition or concentrate, or of the product.

Where the fuel oil composition is produced by incorporation of the additive or concentrate composition, the amount used of each of these compositions will be such as to ensure the incorporation to the fuel oil of the requisite amount of the product. For example, however, the amount of additive or concentrate composition will usually be in the range of 1 to 5,000 ppm (active ingredient) by weight per weight of fuel, especially 10 to 2000 ppm such as 50 to 500 ppm.

What is claimed is:

1. A process for the preparation of monoesters of one or more polyhydroxyalcohols, comprising:

| | |
|---|---|
| (v) | reacting the or each polyhydroxyalcohol with a glyceride ester composition derived from a natural or synthetic source, in the presence of tertiary butanol or tertiary amyl alcohol as reaction medium, and a catalyst; |
| (vi) | if necessary, neutralising the catalyst; |
| (vii) | removing the tertiary butanol or tertiary amyl alcohol; and |
| (viii) | removing the unreacted polyhydroxyalcohol and any liberated glycerol from the product mixture; | characterised in that
in the reaction (i) the polyhydroxyalcohol is present in mass excess relative to the glyceride ester composition: the mass ratio of reaction medium to polyhydroxyalcohol is at least 0.8:1 in the case of tertiary butanol or at least 1.3:1 in the case of tertiary amyl alcohol; the reaction is carried out at a temperature at least equal to the reflux temperature of the reaction medium and at a pressure exceeding 1 bar; and the catalyst is selected from basic salts of Group I and Group II metals and non-metallic nitrogenous bases.

2. The process of claim 1, further characterised in that the alcohol removal step (iv) is conducted by low residence time evaporation, and preferably by thin film evaporation.

3. The process of claim 2, wherein the thin film evaporation is conducted at a temperature of 160 to 200° C. and, preferably, at a reduced pressure of 0.5 to 40 mbar.

4. The process of claim 1, wherein the polyhydroxyalcohol is glycerol.

5. The process of claim 1, wherein the glyceride ester composition reactant is derived from a vegetable source oil and comprises glycerides of unsaturated fatty acids.

6. The process of claim 5 wherein the unsaturated fatty acids comprising the glyceride ester composition reactant include one or more of oleic, linoleic, linolenic and erucic acids.

7. The process of claim 6 wherein the glyceride ester composition reactant is rapeseed oil.

\* \* \* \* \*

UNITED STATES PATENT AND TRADEMARK OFFICE
CERTIFICATE OF CORRECTION

PATENT NO. : 6,664,404 B2
DATED : December 16, 2003
INVENTOR(S) : Graham Jackson It is certified that error appears in the above-identified patent and that said Letters Patent is hereby corrected as shown below:

Column 8,
Line 6, change '(v)" to -- (i) --, "(vi)" to -- (ii) --, "(vii)" to -- (iii) -- and "(viii)" to -- (iv) --.

Signed and Sealed this

Eleventh Day of May, 2004

JON W. DUDAS
*Acting Director of the United States Patent and Trademark Office*